United States Patent [19]

Feiring et al.

[11] Patent Number: 5,196,604
[45] Date of Patent: Mar. 23, 1993

[54] FLUORINATED POLY(ETHER SULFONES)

[75] Inventors: Andrew E. Feiring; Samuel D. Arthur, both of Wilmington, Del.

[73] Assignee: E. I. Du Pont de Nemours and Company, Wilmington, Del.

[21] Appl. No.: 786,677

[22] Filed: Nov. 4, 1991

Related U.S. Application Data

[62] Division of Ser. No. 435,831, Nov. 9, 1989, Pat. No. 5,084,548.

[51] Int. Cl.$^5$ ............................................. C07C 317/06
[52] U.S. Cl. ...................................... 568/34; 568/32; 568/35
[58] Field of Search ............................. 568/35, 34, 32

[56] References Cited

U.S. PATENT DOCUMENTS 3,941,748  3/1976  King ................................... 260/47 R
4,331,798  5/1982  Staniland ............................ 528/125

FOREIGN PATENT DOCUMENTS 243833  4/1986  European Pat. Off.
5165920  6/1979  Japan.
2199622  2/1986  Japan.

OTHER PUBLICATIONS

Smith, C. P., Chemtech, 290–291 (1988), "High Performance Polymers".
Maiti, S. and Mandall, B. K., "Aromatic Polyethers by Nucleophilic Displacement Polymerization", Prog. Polym. Sci., vol. 12, pp. 111–153 (1986).
The Encyclopedia of Polymer Science and Engineering, 2nd Ed., Mark et al., Eds., vol. 13, pp. 196–211, Wiley (1988).
Lai et al., Solid State Technology, pp. 165–170 "Polymers In Electronics" (Nov. 1984).
V. I. Popov et al., Zhurnal Organicheskoi Khimii, vol. 13, No. 10, pp. 2135–2138, Oct. (1977).

Primary Examiner—Marianne M. Cintins
Assistant Examiner—Margaret Page
Attorney, Agent, or Firm—Nancy S. Mayer

[57] ABSTRACT

Polymers comprising fluorine-containing poly(ether sulfones) and monomers comprising aromatic fluorine-containing sulfones used in the preparation of these polymers.

5 Claims, No Drawings

FLUORINATED POLY(ETHER SULFONES)

This is a division of application Ser. No. 07/435,831, filed Nov. 9, 1989, now U.S. Pat. No. 5,084,548.

FIELD OF THE INVENTION

The present invention relates to polymers comprising fluorine-containing poly(ether sulfones) and to the aromatic fluorine-containing sulfone monomers used in the preparation of these polymers.

BACKGROUND OF THE INVENTION

Aromatic poly(ether sulfones) are thermally stable, amorphous engineering resins with attractive properties for electronics and other applications. See C. P. Smith, Chemtech, 290-291 (1988). There resins may be prepared by nucleophilic displacement polymerization of bis-phenols with 4,4'-dihaloaromatic sulfones, where the electronegative sulfone group activates the halides to nucleophilic displacement. Other polymers are also prepared by aromatic nucleophilic substitution with activation provided by a ketone function. A literature review on the synthesis of aromatic polyethers by nucleophilic displacement polymerization, the mechanism of activation of such reactions by various groups, and the properties of polyethers is provided in Maiti, S. and Mandall, B. K., "Aromatic Polyethers by Nucelophilic Displacement Polymerization", Prog. Polym. Sci., Vol. 12, pp. 111-153 (1986).

U.S. Pat. No. 3,941,748 of King issued Mar. 2, 1976, discloses a process for the preparation of an aromatic polymer of recurring units —ArQ— by heating a reaction mixture of an alkali metal fluoride and (a) a halophenol of formula XArQH and/or (b) a mixture of a dihalobenzenoid compound of formula XArX and a dihydric phenol of formula HQArQH in which Ar is a bivalent aromatic residue, Q is an oxygen or sulfur atom, and X is a halogen atom.

U.S. Pat. No. 4,331,798 of Staniland issued May 25, 1982 teaches production of aromatic Polyethers by reacting (a) a mixture of a bisphenol and a dihalobenzenoid compound or (b) a halophenol, in which dihalobenzenoid compound or halophenol halogen atoms are activated by ortho or para —$SO_2$— or —CO— groups, with an alkali metal carbonate in the presence of an infusible particulate support substance.

European Patent Application 243,833 discloses a copolycondensate moulding composition containing polyarylene sulfone and polyarylene ether sulfone units prepared by polycondensation of a bisphenol mixture of bisphenol A; 4,4'-dihydroxydiphenyl sulfone; and other bisphenol and a mixture of 4,4'-bis-halophenyl sulfone and a 4,4'-dihalo-bis-, 4,4''-tris- or 4,4'''-tetrakis-phenyl compound.

Japanese Patent Application J6 2199-622 discloses hydrophilic aromatic sulfone resins prepared by reacting aromatic polysulfone polymers having terminal active releasing groups and hydrophilic compounds having active hydroxy groups to yield ether bonds between the terminal groups of the aromatic polysulfone polymers and the hydrophilic compounds.

Japanese Patent Application J5 5165-920 teaches the production of a linear chlorine-containing polyethersulfone polymer by adding an aromatic tri-or tetrahalide of formula (II):

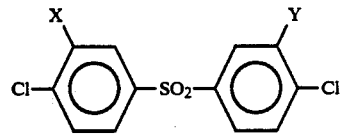

wherein:
X and Y are each H or Cl provided one is Cl, to a mixture of an inert highly polar solvent and a dialkali metal salt of formula (I):

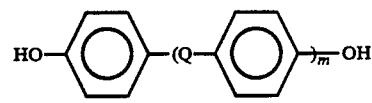

wherein:
Q is a bond, O, S, aliphatic or alicyclic hydrocarbyl and m is 0 or 1.

A discussion of physical, mechanical, thermal, and electrical properties of various commercial polysulfones is provided in the Encyclopedia of Polymer Science and Engineering, 2nd Ed., Mark et al., Eds., Vol. 13, pp. 196-211, Wiley (1988). Prior art polymers are typically amber or yellow in color. For practical applications in electronics, properties such as high resistivity, high breakdown voltage, and low dielectric constant are important. See Lai et al., Solid State Technology, pp. 165-170 (Nov. 1984). A low dielectric constant is particularly desirable in high-speed electrical connections. For practical applications in gas separation techniques, high permeability combined with selectivity is desirable. Thus, there is a need for polysulfones of lower dielectric constant or of high selective permeability. Also, colorless polymers of optical clarity could have many potential applications.

It is therefore an object of the present invention to provide aromatic fluorine-containing poly(ether sulfones) having a low dielectric constant.

It is a further object of the present invention to provide such polymers from which films can be made which are optically clear and colorless.

It is a further object of the present invention to provide such polymers which have good selectivity and permeability to gases.

It is a further object of the present invention to provide aromatic fluorine-containing sulfone monomers used in the preparation of such polymers.

SUMMARY OF THE INVENTION

The present invention comprises an aromatic fluorine-containing poly(ether sulfone) polymer having the following repeating unit (I):

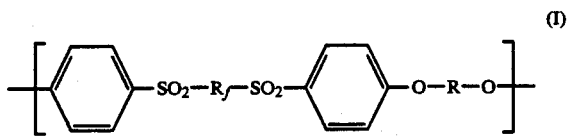

wherein:
$R_f$ is a straight chain or branched polyfluoroalkylene of from 1 to about 20 carbon atoms unsubstituted or substituted by one or more ether oxygens; and
R is an aromatic moiety.

The present invention further comprises a monomer having the following formula (II):

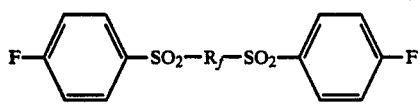

wherein:
R$_f$ is as defined above in formula (I).

DETAILED DESCRIPTION OF THE INVENTION

The present invention comprises novel aromatic fluorine-containing sulfone monomers of formula (II):

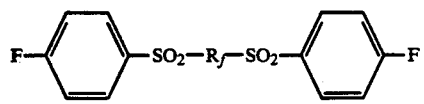

wherein:
R$_f$ is a straight chain or branched polyfluoro alkylene of from 1 to about 20 carbon atoms; or R$_f$ is a straight chain or branched polyfluoroalkylene of from 1 to about 20 carbon atoms substituted by one or more ether oxygens.

Such monomers are useful in the synthesis of aromatic fluorine-containing poly(ether sulfone) polymers.

The monomers of formula (II) can be prepared by the reaction of sodium p-halobenzenethiolates with α, ω-diiodoperfluoroalkanes, followed by oxidation of the resulting sulfides to sulfones with chromium trioxide according to the following reaction sequence wherein X is fluorine.

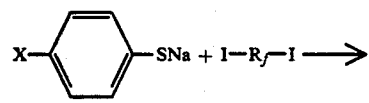

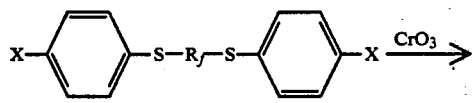

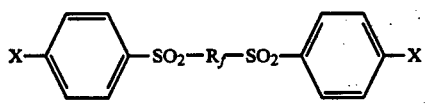

The present invnetion further comprises novel aromatic fluorine-containing poly(ether sulfone) polymers having the following repeating unit (I);

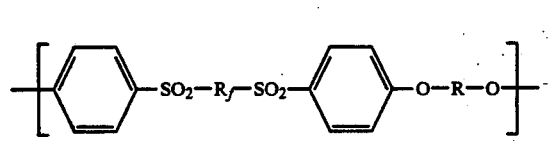

wherein:
Rf is as defined above for formula (II), and
R is an aromatic moiety. Examples of R include aromatic rings, fused aromatic rings such as naphthalene, polyphenyls, biphenyls and the like. R may also be

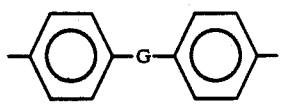

where G is C(CH$_3$)$_2$ or C(CF$_3$)$_2$.

These polymers are prepared by the condensation polymerization of the fluoromonomers of formula (II), or corresponding chloromonomers, with aromatic dihydroxy compounds such as bisphenols, biphenol or hydroquinones according to the following reaction wherein X is fluorine or chlorine:

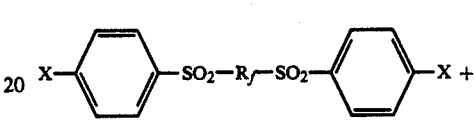

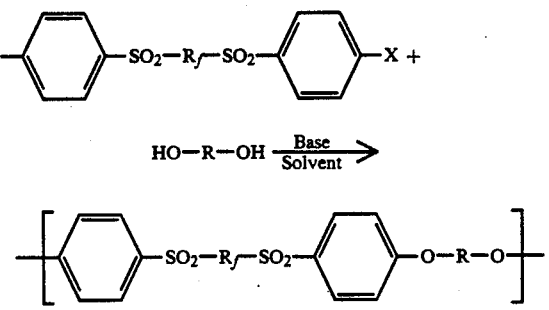

Use of the monomer of formula (II) is preferred since it tends to give a higher yield and higher molecular weight polymer as demonstrated by Examples 6 and 6A. The reaction of the fluoro- or chloromonomer with dihydroxy aromatic compounds may be conducted under a variety of conditions in the presence of a base of sufficient strength to cause substantial ionization of the dihYdroxy aromatic compound. Typical bases are the alkali metal carbonates, hydrogen carbonates and hydroxides. Preferred bases are the alkali metal carbonates; the most preferred base is sodium carbonate. Alternatively, the dihydroxy aromatic compound may be converted to its bis-alkali metal salt in a separate step and then reacted with the monomer. The reaction is preferably conducted in a solvent such as a dipolar aprotic organic solvent. Preferred solvents are dimethyl formamide, dimethyl acetamide, diphenyl sulfone and dimethyl sulfoxide, and mixtures of these solvents with each other or other aprotic organic solvents. The most preferred solvent is a mixture of dimethyl acetamide and toluene.

The reaction time and temperature may be varied depending on the nature of the base and dihydroxy aromatic compound and the desired polymer molecular weight. Using the preferred sodium carbonate base in excess and a mixture of dimethyl acetamide and toluene as solvent, high molecular weight polymers from the monomer of formula (II) and dihydroxy aromatic compounds can be achieved in less than about 2 hours at a reaction temperature of about 140° C. Optionally, a neutralizing agent such as dimethyl sulfate may be added at the end of the reaction time to cap unreacted hydroxy groups.

The polymers of this invention are useful for forming molded objects and chemically stable films, such as those used in gas separating membranes and other applications. They typically have a dielectric constant less than 3, a high rate of permeability with high selectivity, as well as excellent mechanical properties. Films and membranes made from these polymers are optically clear and colorless.

The following examples demonstrate the monomers and polymers of the present invention but are not intended to limit it in any manner. The polymerization solvents, dimethylacetamide (DMAC) and toluene, used in these examples were distilled under argon at atmospheric pressure, stored under argon until used, and transferred using syringe techniques. Bisphenol-A (4,4'-isopropylidenediphenol), a polymerization grade material from E. I. du Pont de Nemours and Company, Wilmington, Delaware, was dried at 0.25 mm. 4,4'-Diphenol (Aldrich Chemical Company, Milwaukee, Wisconsin) was recrystallized twice from ethanol. Bisphenol-AF (2,2-bis(4-hydroxy phenyl)hexafluoropropane) was sublimed twice at 165°-170° C. and 0.1 mm and recrystallized from $CHCl_3/CCl_4$. Diiodoperfluoroalkanes were prepared according to a known procedure (C. D. Bedford and K. Baum, J. Org. Chem., 1980, 45, 347, herein incorporated by reference). 1,8-bis-(4-chlorophenylsulfonyl)-perfluorooctane was prepared according to procedures described in V. I. Popov et al., J. Org. Chem., USSR (Engl. Trans.) 1977, 13, 1985, herein incorporated by reference. All other materials were obtained from commercial sources and used as received.

EXAMPLE 1

Synthesis of

1,4-bis-(4-fluorophenylthio)perfluorobutane

To a solution of 14 g (0.7 mol) sodium 4-fluorophenylthiolate in 500 mL dimethylformamide, under $N_2$ and at 0° C., was added 150 g (0.33 mol) of 1,4-diiodoperfluorobutane, resulting in an exotherm to 40° C. The resulting mixture was stirred overnight at room temperature, then heated to 60° C. for one hour. The solution at room temperature was diluted with 200 mL water and concentrated on a rotary evaporator to remove about 300 mL of solvent. The remaining solution was diluted with water, the lower layer was separated and washed with water. The produce was bulb-to-bulb distilled at 120° C. and 0.5 mm. After removal of low boiling impurities, the colorless liquid product was collected, 129.7 g (86%). Spectral data obtained on another sample prepared in the same fashion, showed:

$^1$H-NMR ($CDCl_3$) δ 7.10 (m, 4H); 7.63 (m, 4H).
$^{19}$F-NMR ($CDCl_3$) δ —85.9 (t, 4F); —117.3 (t, 4F); —107.3 (m, 2F).

EXAMPLE 2

Synthesis of

1,8-bis(4-fluorophenylthio)perfluorooctane

To a solution of 27.3 g (0.18 mol) of sodium 4-fluorophenylthiolate in 400 mL of dimethylformamide was added 54 g (0.083 mol) of 1,8-diiodoperfluorooctane. The resulting solution was warmed to 52° C. for 4 hours, then concentrated on a rotary evaporator. The residue was added to ice water and a precipitate was collected. The aqueous solution was extracted with 2×400 mL of ether. The precipitate was dissolved in the combined ether extracts, washed with saturated aqueous $Na_2CO_3$ solution and brine, and dried over $MgSO_4$. The ether solution was evaporated and the residue was distilled in a Kugelrohr apparatus to give 81% of product, distilling at 133° C. and 0.1 mm. Another sample prepared in a similar fashion showed m.p.=60°-61° C. and had the following spectral data:

$^1$H-NMR ($CDCl_3$) δ 7.11 (m, 4H); 7.68 (m, 4H).
$^{19}$F-NMR ($CDCl_3$) δ —87.5 (t, 4F); —119.4 (m, 4F); —121.4 (m, 2F); —121.9 (m, 4F); —108.9 (M, 2F)

EXAMPLE 3

Synthesis of

1,4-bis(4-fluorophenylsulfonyl)perfluorobutane

A solution of 129.7 g (0.285 mol) of 1,4-bis(4-fluorophenylthio)perfluorobutane, 175 g chromium trioxide and 1.5 L acetic acid was refluxed for 8 hours. An additional 50 g of chromium trioxide were added and reflux was maintained overnight. After cooling to room temperature, 100 mL of water were added and the solution was concentrated not quite to dryness on a rotary evaporator. The residue was added to ice water and filtered. The solid was dissolved in methylene chloride, washed with water, and concentrated to dryness under reduced pressure. The resulting solid was recrystallized from ethyl acetate/hexane to give in three crops 135 g (92%) of product, m.p. 126°-127° C. Another sample prepared in the same fashion showed:

$^1$H-NMR ($CDCl_3$) δ 7.14 (m, 4H); 8.1 (m, 4H).
$^{19}$F-NMR ($CDCl_3$) δ —110.4 (m, 4F); —118.8 (m, 4F); —96.7 (m, 2F).

Analysis Calculated for $C_{16}H_8F_{10}O_4S_2$:
C, 37.07; H, 1.56; F, 36.56; S, 12.37.
Found: C, 37.07; H, 1.61; F, 37.35; S, 12.66.

EXAMPLE 4

Synthesis of

1,8-bis-(4-fluorophenylsulfonyl)perfluorooctane

A solution of 6.0 g (0.092 mol) of 1,4-bis(4-fluorophenylthio)perfluorooctane in 100 mL of acetic acid was treated portionwise with 7.0 g chromium trioxide. The solution was refluxed for 3 hours. About 60% of the acetic acid was removed by distillation and the residue was poured into ice water. The aqueous solution was extracted with ether which was washed with water, saturated aqueous $Na_2CO_3$ and brine, and evaporated. The residue was dissolved in a boiling mixture of $CH_2Cl_2$ and hexane and cooled to 0° C. to give 5.9 g (89%) of product, m.p. 109°-110° C.

$^1$H-NMR ($CD_2Cl_2$) δ 7.4 (m, 4H); 8.1 (m, 4H).
$^{19}$F-NMR ($CD_2Cl_2$) δ —111.5 (m, 4F); —120.0 (m, 4F); —121.7 (m, 8F); —98.2 (m, 2F).

Analysis Calculated for $C_{20}H_8F_{18}O_4S_2$:
C, 33.44; H, 1.12 F, 47.61; S, 8.93.
Found: C, 33.47; H, 1.17; F, 47.40; S, 9.18.

EXAMPLE 5

Polymerization of 1,8-bis-(4-fluorophenylsulfonyl) perfluorooctane with bisphenol-A A flask equipped for azeotropic distillation and magnetic stirring was dried under nitrogen and charged with 1.7 g powdered potassium carbonate, 1.14 g (0.05 mol) bisphenol-A, 25 mL toluene and 25 mL dimethyl acetamide. The mixture was heated to a pot temperature of 138° C. to azeotropically remove water. It was cooled to 75° C. and 3.59 g (0.05 mol) of 1,8-bis-(4-fluorophenylsulfonyl)perfluorooctane was added. The resulting mixture was heated to 138°-142° C. overnight. The mixture was poured into water. The polymer was isolated, washed with water and dissolved in $CH_2Cl_2$. This solution was filtered and evaporated. The resulting solid was dissolved in 125 mL of CH$_2$Cl$_2$ and poured into 500 mL of stirred methanol to give 2.2 g of polymer showing the following properties:

$\eta_{inh}$ (DMAC), inherent viscosity,=0.29; T$_g$, glass transition temperature by differential scanning calorimetry=107° C.

$^1$H-NMR (CD$_2$Cl$_2$) δ 1.75 (s, 6H); 7.05 (d, 4H); 7.15 (d, 4H); 7.35 (d, 4H); 7.95 (d, 4H).

$^{19}$F-NMR (CD$_2$Cl$_2$) δ −111.0 (4F); −119.2 (4F); −120.9 (8F).

Analysis Found: C, 46.41;1 H, 2.52; F, 34.00; S, 7.45.

EXAMPLE 6

Polymerization of 1,8-bis-(4-fluorophenylsulfonyl) perfluorooctane with bisphenol-A A 50 mL flask equipped for azeotropic distillation and mechanical stirring was dried under nitrogen and charged with 0.84 g (0.0037 mol) bisphenol-A, 1.17 g sodium carbonate, 2.7 g (0.0037 mol) of 1,8-bis-(4-fluorophenylsulfonyl)perfluorooctane, 30 mL dimethyl acetamide, and 5 mL toluene. The mixture was heated to 100° C. and held for about 15 minutes, then heated to about 140° C. and held for about 70 minutes. An additional 10 mL of dimethyl acetamide were added, the viscous mixture was cooled to 130° C. and 4 mL of dimethylsulfate were added. The mixture was added to ice cold dilute aqueous HCl. The precipitated polymer was washed with water and methanol, and dissolved in CH$_2$Cl$_2$. This solution was filtered and poured into hexane to give 2.85 g (86%) of polymer showing the following properties:

$\eta_{inh}$ (DMAC), inherent viscosity,=1.75; T$_g$, glass transition temperature by differential scanning calorimetry=124° C.

A film cast from 1,1,2-trichloroethane and dried at 100° C. showed the following mechanical properties: Tensile at break=6.6 Kpsi; Elongation at break=4%; Tensile modulus=194 Kpsi.

Another sample prepared by a similar procedure had $\eta_{inh}$ (CH$_2$Cl$_2$), inherent viscosity,=1.29.

By gel permeation chromatography, this material had a weight average molecular weight, M$_w$, =3.7×10$^5$; number average molecular weight, M$_n$=1.3×10$^5$; and polydispersity, M$_w$/M$_n$, =2.75. By laser light scattering at 25° C. in CH$_2$Cl$_2$, it showed a weight average molecular weight, M$_w$=9.8×10$^5$.

COMPARATIVE EXAMPLE 6A

Polymerization of 1,8-bis-(4-chlorophenylsulfonyl) perfluorooctane with bisphenol-A The procedure of Example 6 was followed on a 0.004 molar scale giving 2.12 g of polymer with $\eta_{inh}$ (CH$_2$Cl$_2$), inherent viscosity,=0.074. This example demonstrates that the chloro compound polymerizes less efficiently than the fluoro compound.

EXAMPLE 7

Polymerization of 1,4-bis-(4-fluorophenylsulfonyl) perfluorobutane with bisphenol-A The procedure of Example 6 was followed giving 2.29 g (88%) of polymer showing the following properties:

$\eta_{inh}$ (CH$_2$Cl$_2$), inherent viscosity,=0.951; T$_g$, glass transition temperature by differential scanning calorimetry=142° C.

$^1$H-NMR (CD$_2$Cl$_2$) δ 1.73 (s, 6H); 7.05 (d, 4H); 7.15 (d, 4H); 7.35 (d, 4H); 7.92 (d, 4H).

$^{19}$F-NMR (CD$_2$Cl$_2$) δ −111.8 (4F); −119.9 (4F).

Analysis Found: C, 52.44; H, 3.03; F, 20.85; S, 9.41.

A film cast from 1,1,2-trichloroethane and dried at 100° C. showed mechanical properties: Tensile at break=5.4 Kpsi; Elongation at break=2.5%; Tensile modulus=178 Kpsi. Gel permeation chromatography: M$_w$, weight average molecular weight,=2.28×10$^5$; M$_n$, number average molecular weight,=9.5×10$^4$;

Polydispersity, M$_w$/M$_n$,=2.4. Laser light scattering: M$_w$, weight average molecular weight,=2.05×10$^5$.

EXAMPLE 8

Polymerization of 1,4-bis-(4-fluorophenylsulfonyl) perfluorooctane with 4,4'-biphenol The procedure of Example 6 on a 0.0027 mol scale was followed. This polymer is insoluble in CH$_2$Cl$_2$, so it was washed with this solvent and dried, giving 2.17 g (93%) of polymer showing the following properties: $\eta_{inh}$ (DMAC), inherent viscosity,=1.24; T$_g$, glass transition temperature by differential scanning calorimetry,=145° C.

Another sample prepared by a similar procedure had $\eta_{inh}$, inherent viscosity,=0.648.

Analysis Found: C, 43.96; H, 1.74; F, 38.58; S, 7.64.

A film cast from dimethyl acetamide and dried at 150° C. showed mechanical properties: Tensile at break=4.8 Kpsi; Elongation at break=6.4%; Tensile modulus=128 Kpsi.

EXAMPLE 9

Polymerization of 1,4-bis-(4-fluorophenylsulfonyl) perfluorobutane with 4,4'-biphenol The procedure of Example 6 was followed on a 0.0029 molar scale giving 1.64 g (85%) of polymer showing the following properties: $\eta_{inh}$ (DMAC), inherent viscosity,=1.36; T$_g$, glass transition temperature by differential scanning calorimetry,=162° C.

$^1$H-NMR (CD$_2$Cl$_2$) δ 7.22 (dd, 8H); 7.68 (d, 4H); 7.97 (d, 4H).

$^{19}$F-NMR (CD$_2$Cl$_2$) δ −111.7 ( (4F); −119.8 (4F).

Analysis Found: C, 49.91; H, 2.32; F, 20.41.

A film, prepared from several polymer samples, cast from tetrachloroethane and dried at 105° C. showed mechanical properties: Tensile at break=7.9 Kpsi; Elongation at break=5.1%; Tensile modulus=183 kpsi.

EXAMPLE 10

Polymerization of 1,8-bis-(4-fluorophenylsulfonyl) perfluorooctane with bisphenol-AF The procedure of Example 6 was followed on a 0.0046 molar scale giving 4.19 g (92%) of polymer showing the following properties:

$\eta_{inh}$ (CH$_2$Cl$_2$), inherent viscosity,=0.149; T$_g$, glass transition temperature by differential scanning calorimetry,=114° C.

$^1$H-NMR (CD$_2$Cl$_2$) δ 7.17 (d, 4H); 7.22 (d, 4H); 7.52 (d, 4H); 8.0 (d, 4H).

$^{19}$F-NMR (CD$_2$Cl$_2$) δ −64.19 (6F); −111.8 (4F); −119.98 (4F); −121.8 (8F).

EXAMPLE 11

Polymerization of 1,4-bis-(4-fluorophenylsulfonyl) perfluorobutane with hydroquinone The procedure of Example 6 was followed on a 0.0062 molar scale. This polymer is insoluble in $CH_2Cl_2$ so it was washed with this solvent and dried, giving 3.21 g (88%) of polymer showing the following properties: $\eta_{inh}$ (DMAC), inherent viscosity, =0.45; $T_g$, glass transition temperature by differential scanning calorimetry, =146° C.

EXAMPLE 12

Polymer Properties

Properties of the polymers of Examples 6–11 are summarized in Table 1. The polymers were isolated as white solids, soluble in dimethyl acetamide and chlorinated hydrocarbons and insoluble in hexane, acetone or methanol. The biphenyl-based polymers were somewhat less soluble in the chlorinated hydrocarbons than the bisphenol-A analogs. Glass transition temperatures, as measured by differential scanning calorimetry, range from 114° C. to 165° C. All polymers showed good thermal stability with thermal gravimetric analysis decomposition temperatures under nitrogen of about 400° C. The high molecular weight polymers of Examples 6, 7, 8 and 9 gave clear, colorless and flexible films from the melt or solution casting with tensile properties shown in Table 1.

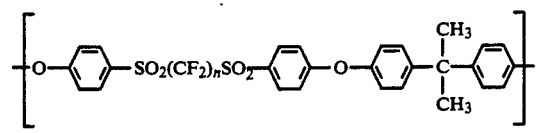

Example 6, n = 8
Example 7, n = 4.

Effects of fluorinated groups on the electrical properties of polymers are of interest, since a low dielectric constant is a desirable feature in various microelectronic applications. Dielectric properties of the polymer of Example 6 were measured. A film of the polymer was laminated between 1 ounce copper foils at 270° C. and 1000 psi, resulting in good adhesion of the film to copper. The laminate was etched on one side to give a serpentine pattern. The dielectric constant and dissipation factor were determined by time domain reflectometry, Measurements were made over the frequency range of 50 MHz to 10 GHz using a Hewlett-Packard 8150B Network Analyzer, 8340B Synthesized Sweeper and 8515A S-Parameter Test Set. Samples were placed in a precision machined fixture with micrometer positioning in all axes. The test fixture uses a set of metrology grade, high precision Eisenhart Launchers (EL 18) manufactured by Cascade Microtech Co. with sexless APC-7 connectors which permit the transition from coaxial to planar geometry while preserving 50 ohm impedance.

TABLE 1

Properties of Fluorinated Poly(ether sulfones)

| Ex. | Yield | $T_g{}^a$ | $T_d{}^b$ | $\eta_{inh}{}^c$ (solvent) (dL/G) | $GPC^d$ $M_n$ | $M_w$ | Tensile$^e$ T(Kpsi)/E(%)/ M(Kpsi) |
|-----|-------|-------|-------|--------------|--------|--------|---------|
| 6 | 86% | 124° C. | 411° C. | 1.75($CH_2Cl_2$) | | | 6.6/4.0/194 |
|   |     |         |         | 1.29($CH_2Cl_2$) | 130000 | 370000 | |
| 7 | 88% | 142° C. | 400° C. | 0.95($CH_2Cl_2$) | 95000 | 228000 | 5.4/2.5/178 |
| 8 | 93% | 145° C. | 405° C. | 1.24(DMAC)$^f$ | | | 4.8/6.4/128 |
| 9 | 85% | 162° C. | 408° C. | 1.36(DMAC) | 191000 | 363000 | 7.9/5.1/183 |
| 10 | 92% | 114° C. | 408° C. | 0.15($CH_2Cl_2$) | | | |
| 11 | 88% | 141° C. | 400° C. | 0.46(DMAC) | | | |

$^a$Glass transition temperature by differential scanning calorimetry.
$^b$Temperature of 10% weight loss by thermogravimetric analysis nitrogen.
$^c$Inherent viscosity using polystyrene standard.
$^d$Gel permeation chromatography, Mn - number average molecular weight,; Mw = weight average molecular weight.
$^e$T = tensile strength; E. = % elongation; M = modulus.
$^f$DMAC = dimethyl acetamide.

Properties of the polymers of Examples 6 and 7 may be compared with the commercially available Udel ® poly(ether sulfone) which lacks the fluorinated spacer groups. Incorporation of the flexible fluorinated spacer group lowers the glass transition temperatures of the polymer of Example 6 (123° C.) and Example 7 (142° C.) as compared to Udel ® (195° C.). Tensile strength and modulus are comparable.

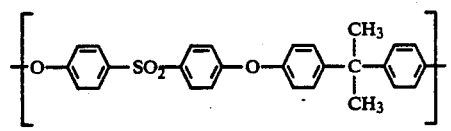

Udel ®

(Electrical performance data for the launchers follows: Frequency range—dc to 18 GHz, Insertion Loss −0.10 db max to 10 GHz and 0.25 db max to 18 GHz, VSWR −1:15:1 max (23 db return loss). The samples for measurement measured 2"×2" and consisted of a 14 bend serpentine "meander" with 67 cm circuit length and 610 micron trace width on one side of the sample and a ground plane of copper on the other side. The measured value of the dielectric constant was 2.76 and the dissipation factor was 0.011. The reported dielectric constant for Udel ® is 3.19 (Encyclopedia of Polymer Science and Engineering, 2nd Ed., Mark et al., Eds., Vol. 13, pp. 192–211, Wiley, 1988).

EXAMPLE 13

Permeability Properties of Fluorinated Poly(ether sulfone) Membranes

Fluorinated poly(ether sulfone) film for gas permeation testing was produced by spreading a chloroform solution (10% w/v) onto a clean glass plate with a doctor knife (15-mil knife clearance). The cast film was allowed to stand covered at room temperature for several hours and was then heated in a vacuum oven (100° C.) overnight to remove traces of solvent. The film was stripped from glass by immersion in water and was allowed to dry in air at room temperature for a day before testing.

A modified Millipore high pressure filter holder accepting a 47-mm circle of polymer film was used for permeation testing. The filter holder was modified so that the high pressure side could be continuously swept with the feed gas. The film was pressurized with oxygen/nitrogen (21:79 molar volume) at 500 psig and the gas permeation rate was measured by volume displacement at 1 atm of a water droplet in a capillary tube. Permeate gas composition was determined by evacuating the permeate side of the membrane to 5-10 mm Hg with a vacuum pump through a gas chromatograph sample loop (0.10 mL sample volume; Varian 3700 GC with a 6′×⅛″ 60-80 mesh 5A molecular sieve column; 60° C.; $O_2/N_2$ detector response ratio=0.96). Measurements were typically taken over several hours to ensure steady state permeation conditions. Calculations were performed according to the method of W. J. Ward III et al., Ultrathin Silicone/Polycarbonate Membranes for Gas Separation Process, J. Membrane Sci., 1 (1976) 99, hereby incorporated by reference. The resulting test data is summarized in Table II.

TABLE II

| Polymer Structure | Film Thickness mil | Permeation Rate cc/min | $O_2$ % | Ratio of Permeability of $O_2/N_2$ | Permeability $O_2$, cB* |
|---|---|---|---|---|---|
| Example 6 | 0.8 | 0.093 | 53.1 | 4.44 | 230 |
| Example 7 | 1.2 | 0.023 | 60.3 | 5.95 | 100 |
| Example 7 | 0.7 | 0.056 | 62.5 | 6.53 | 150 |
| Example 9 | 0.8 | 0.037 | 55.8 | 4.95 | 100 |

*cB = centiBarrers = $\dfrac{10^{-12} cm^3 (STP) \cdot cm}{cm^2 \cdot sec \cdot cm\ Hg}$

What is claimed is:

1. A compound of formula (II)

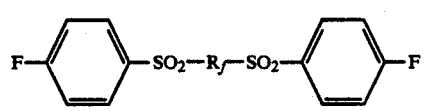

(II)

wherein:
$R_f$ is a straight chain or branched polyfluoroalkylene of from 1 to about 20 carbon atoms unsubstituted or substituted with one or more ether oxygens.

2. A compound of claim 1 wherein $R_f$ is a straight-chain or branched perfluoroalkylene group.

3. A compound of claim 2 wherein $R_f$ is $(CF_2)_n$ and n is 2 to 20.

4. A compound of claim 1 which is 1,4-bis-(4-fluorophenylsulfonyl)perfluorobutane.

5. A compound of claim 1 which is 1,8-bis-(4-fluorophenylsulfonyl)perfluorooctane.

* * * * *